United States Patent [19]
Ciobanu

[11] Patent Number: 5,820,263
[45] Date of Patent: Oct. 13, 1998

[54] APPARATUS AND METHOD FOR MONITORING THE TEMPERATURE OF A REGION OF HUMAN TISSUE

[76] Inventor: Sorin G. Ciobanu, 5101 Crooks Rd., Apt. 8, Royal Oak, Mich. 48073

[21] Appl. No.: 976,629

[22] Filed: Nov. 24, 1997

Related U.S. Application Data

[63] Continuation-in-part of Ser. No. 680,180, Jul. 15, 1996, abandoned.

[51] Int. Cl.⁶ .............. G01K 3/14; G01K 3/06; G01K 7/22; G01J 5/02; A61B 5/00
[52] U.S. Cl. ............... 374/111; 374/112; 374/128; 374/183; 374/121; 600/549; 600/474
[58] Field of Search .................... 374/121, 124, 374/128, 112, 111, 166, 183; 600/549, 474

[56] References Cited

U.S. PATENT DOCUMENTS

| | | | |
|---|---|---|---|
| 3,719,071 | 3/1973 | Hohenberg | 374/111 |
| 3,830,224 | 8/1974 | Vanzetti et al. | 374/162 |
| 3,847,139 | 11/1974 | Flam | 374/162 |
| 3,935,460 | 1/1976 | Flint | 374/112 |
| 4,190,053 | 2/1980 | Sterzer | 374/112 |
| 4,316,175 | 2/1982 | Korber et al. | 374/112 |
| 4,324,138 | 4/1982 | Davis et al. | 374/111 |
| 4,440,509 | 4/1984 | Agarwal | 374/111 |
| 4,699,519 | 10/1987 | Persson | 374/111 |
| 4,773,766 | 9/1988 | Nagasaka et al. | 374/112 |
| 4,874,253 | 10/1989 | Pompei et al. | 374/121 |
| 5,046,858 | 9/1991 | Tucker | 374/179 |
| 5,165,794 | 11/1992 | Ortiz | 374/137 |
| 5,562,345 | 10/1996 | Heyman et al. | 374/124 |

FOREIGN PATENT DOCUMENTS

| | | | |
|---|---|---|---|
| 0116873 | 10/1978 | Japan | 374/112 |
| 0121122 | 9/1980 | Japan | 374/111 |
| 0117132 | 9/1981 | Japan | 374/112 |
| 406142061 | 5/1994 | Japan | 600/549 |

*Primary Examiner*—Diego F. F. Gutierrez
*Attorney, Agent, or Firm*—Young & Basile, P.C.

[57] ABSTRACT

An apparatus and method for monitoring a temperature around a point of clinical interest. The apparatus has a sensing surface carrying a plurality of temperature detectors in a regular spatial outer disposition around a central detector. A signal processor computes the highest temperature difference between any two outer detectors and the central detector and compares the highest difference with a predetermined number of temperature domains or ranges. The signal processor activates an output device to provide an indication of the correlation between the highest determined temperature difference and the temperature domains. The output device comprises three different colored lights to provide an indication of normal, doubtful or abnormal correlation. In another embodiment, the output device is a graphical display having a pattern of the organ to be examined as a background and a luminous point on the display, which is either not lit, flashes with a low frequency, or is continuously lit. In another embodiment, the output device is an acoustical device with three different tonalities or sound patterns.

13 Claims, 2 Drawing Sheets

APPARATUS AND METHOD FOR MONITORING THE TEMPERATURE OF A REGION OF HUMAN TISSUE

CROSS REFERENCE TO CO-PENDING APPLICATION

This application is a continuation-in-part of application Ser. No. 08/680,180 filed Jul. 15, 1996, now abandoned in the name of S. Ciobanu and entitled "Apparatus For Early Detection Of Pathologic Underskin Modification".

BACKGROUND OF THE INVENTION

1. Field of the Invention

The present invention relates generally to detection devices and pertains, more specifically, to an apparatus for the measuring and display of the temperature distribution on a specific area of the skin surface.

2. Description of the Art

Temperature measurement is commonly used with medical purposes. The abnormal activity of a group of living human cells is accompanied locally by a thermal activity which differentiates the said group of cells from the contiguous and closely adjacent tissue.

Thermography has been used in medical diagnosis and special devices have been developed which can scan a surface area to produce a thermogram, (photography, computer graphics), containing information pertaining to temperature variations over the scanned area. A localized elevation of temperature can indicate the presence of a cancer, however, such hot spots can be the result of other causes and additional investigation is required to determine the actual cause. The technique requires exceptionally expensive equipment and trained technicians.

U.S. Pat. No. 3,847,139 discloses a device for aid in detecting breast cancer with a waist-like structure including a substrate of conformable material carrying a temperature responsive coating. However this structure has to be worn over the breasts for long periods of time, which is sometimes uncomfortable, the evaluation is made visually and presents the inconvenient that the liquid crystal can come in contact with the skin.

SUMMARY OF THE INVENTION

The present apparatus is a portable, noninvasive, easy to use means for the early detection of such an underskin thermal activity. It is applied with a predetermined regularity on the skin domain to be tested and outputs a signal correlated with the detected thermal activity: normal; doubtful; abnormal.

The apparatus has a set of thermal sensors with a specific spatial positioning on a sensing surface. When the sensing surface is put in contact with a region of the skin, each sensor detects the local temperature below it, being sensitive to the thermal radiation perpendicular on the skin surface. An electronic device computes the highest difference between any two individual sensors and compares the highest difference with one or more predetermined temperature thresholds. An output device provides an indication of the correlation between the highest difference in temperature and the one or more thresholds. The output device can be:

a LED display showing three colored light emitting diodes (LEDs), with green, yellow and red LEDs signifying normal; doubtful; abnormal conditions;

a graphical display, for example a graphical liquid crystal display, having as a background the pattern of the organ to be examined and a luminous point flashing with a low frequency (1 Hz to 18 Hz) or continuously lit, signifying normal; doubtful; abnormal conditions; or an acoustical device with three different tonalities signifying normal; doubtful; abnormal conditions.

This invention refers to an apparatus for a quick, convenient examination which can be made by a person in her own home. The method is totally non interactive with the tissue. It indicates a modification in the intensity of the thermal radiation of a group of human cells contrasting with the same radiation of the tissue surrounding that group of cells, and thus the probability of a local pathological development.

BRIEF DESCRIPTION OF THE DRAWINGS

The foregoing and other objects, features and advantages of the present invention will be apparent from the following more particular description of preferred embodiment of the invention, as illustrated in the accompanying drawings in which like reference characters refer to the same parts throughout the different views in which.

BRIEF DESCRIPTION OF THE PREFERRED EMBODIMENTS

Figure 2:
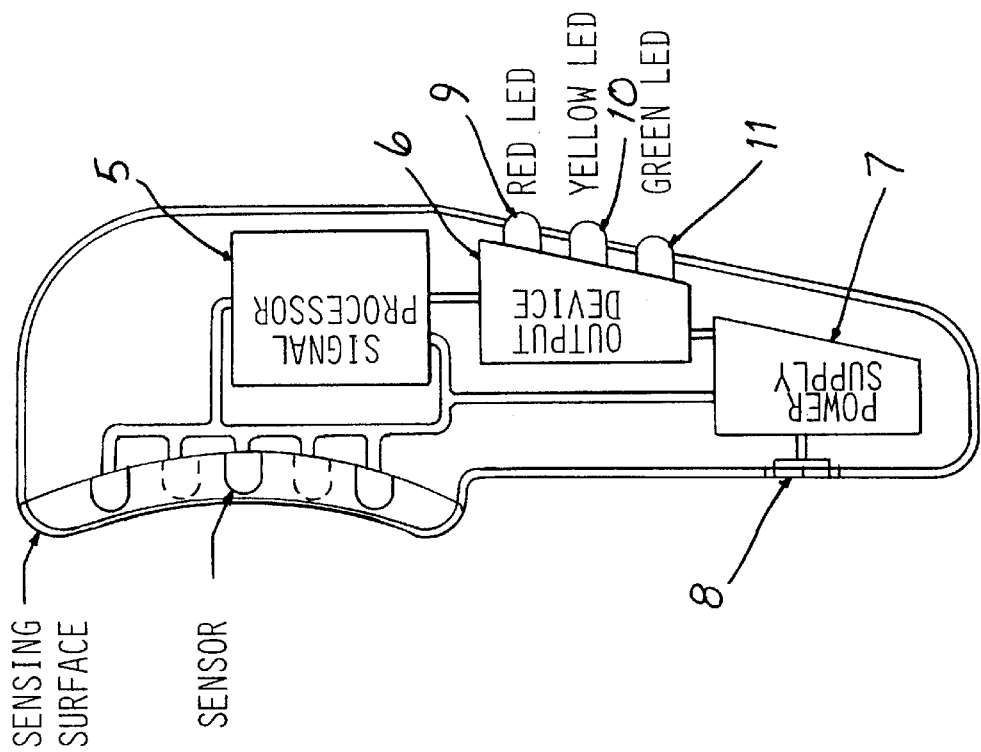
FIG. 2 is the schematic cross-section of the apparatus of FIG. 1 with the three LED output device.
Figure 1:
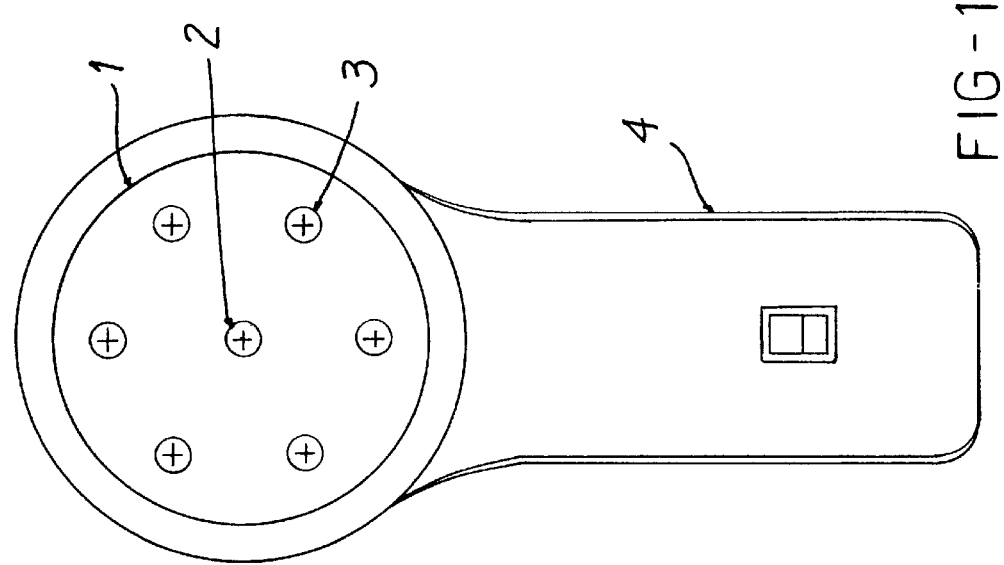
FIG. 1 is the front elevational view of one embodiment of the apparatus using near infrared photodiodes as sensors.
Figure 3:
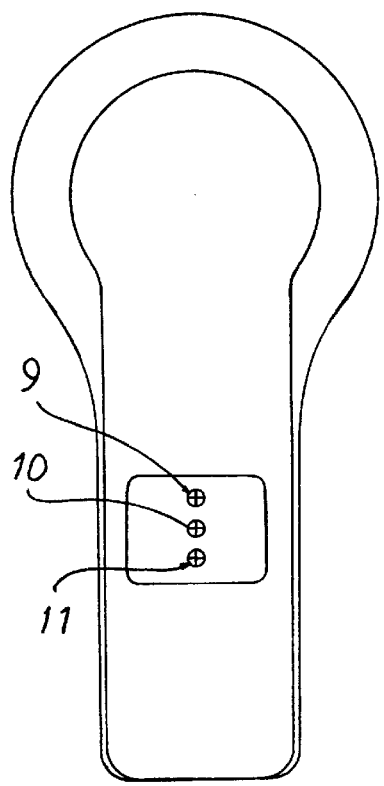
FIG. 3 is a rear elevational view of the embodiment of the apparatus with the three LED output device.

For the detection of a temperature distribution around a point of clinical interest, the apparatus of the present invention utilizes a sensing surface 1 mounted to a circular wall of the casing 4, which houses a signal processor 5, output devices 6, power supply 7, and an on/off switch 8. A temperature sensing device or detector 2 is mounted in the center of the sensing surface 1. A plurality of additional temperature sensing devices or detectors 3 are spaced from the center detector 2 and mounted on or in sensing surface 1. Preferably, the detectors 3 are equidistantly mounted about the center detector 2 in a predetermined spatial configuration. The detectors 3 may be arranged in accordance with a regular geometrical figure, such as an equilateral, square, pentagon, hexagon, octagon, etc. Alternately, as shown in FIG. 1, the detectors 3 can be arranged in a circle about the center detector 2. At least two detectors 3 are provided about the center detector 2, preferably on opposed sides of the center detector 2. Up to eight or more detectors 3 may be provided on the sensing surface 1, with six detectors 3 being shown by way of example only in FIG. 1. The detectors 2, 3 are disposed on the sensing surface 1 so as to have a maximum response at the radiation incidence perpendicular to the skin surface, within an acceptable solid angle of less then 30°. The detectors 2, 3 can be any suitable temperature sensing device, such as thermistors, and, more specifically, glass encapsulated thermistors, with an interchangability tolerance to +0.1° C. over a temperature range from 0° to 70° C. Optoelectronic near infrared detectors which are sensitive to radiation in the 0.8 μm to 1.8 μm wavelength region and a peak spectral response somewhere between 1.5 μm and 1.6 μm can also be employed.

The signals generated by the detectors 2 and 3 are input to the signal processor 5 which may include signal conditioners for each detector 2, 3.

The signal generated by the detectors 2 and 3 can typically be a voltage signal whose magnitude is proportional to the magnitude of the temperature sensed by each detector 2 and 3.

The signal processor 5, which may be any suitable microcontroller, microprocessor or other central processing unit, executes a control program stored in a memory, not shown, which controls the operation of the apparatus. In general, the control program executed by the signal processor enables the signal processor 5 to compare each of the output signals generated by the detectors 3 with the output signal generated by the detector 2 and to calculate a difference between the temperatures represented by the output signals of each detector 3 and the center detector 2. The signal processor 5 then determines which of the calculated temperature differences between one outer detector 3 and the center detector 2 is highest. This highest temperature difference for one pair of detectors 2 and 3 is then compared with threshold value(s) stored in the memory. At least one and preferably two or more thresholds are employed in the present apparatus. The thresholds may be in the form of stored voltage values corresponding to the output signals generated by the detectors 2 and 3 and representative of sensed temperature differences between one pair of detectors 2 and 3. For example, a first or lower threshold may be set at a value corresponding to a temperature difference of 0.2° C. A second higher threshold may be set with a value corresponding to a temperature difference of 0.5° C. The use of two thresholds forms three distinct temperature domains or ranges. The first domain is between 0° C. and the first threshold of 0.2° C. and signifies a normal condition. The second domain between 0.2° C. and 0.5° C. is known as a doubtful domain as described hereafter. The third domain is temperature differences greater than 0.5° C. which represent an abnormal condition. It will be understood that additional thresholds may be employed in the present apparatus. Alternately, graduated thresholds between any two thresholds, such as the first and second thresholds, may also be employed for finer resolution of a detected condition.

The signal processor 5 compares the selected highest temperature difference with the first and second threshold values and determines into which temperature domain the selected highest temperature difference falls. Depending upon where the highest temperature difference falls with respect to the thresholds, the signal processor 5 activates an output means or device 6.

The output device 6 can be an optical or acoustical means able to emphasize a plurality of three different levels of information, i.e., normal; doubtful; abnormal. The output device(s) 6 can be an LED display assembly mounted on the back of the casing 4 and showing a green LED 11 for "normal", a yellow LED 10 for "doubtful" and a red LED 9 for "abnormal". Of course, suitable output drivers may be employed between the signal processor 5 and each output device or LED 6 to provide activation of each LED.

Figure 4:
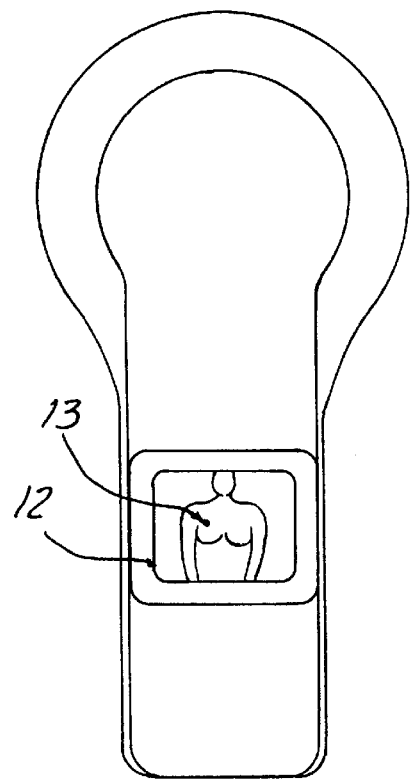
FIG. 4 is a rear elevational view of the apparatus with a graphical display output device.

The output device may also be a graphical display 12, for example, a graphical liquid crystal display module, having as a background or template the pattern of the organ to be examined and a luminous point 13 flashing with a low frequency (1 Hz to 18 Hz) or continuously lit, with the same related meanings, i.e., off for "normal", flashing for "doubtful" and continuously lit for "abnormal". The graphical display shown in FIG. 4 is for use of the present apparatus in detecting breast cancer. It will be understood that a different pattern or template may be placed on or displayed by the liquid crystal display 12 when the apparatus is specifically designed for use in detecting other cancers or abnormalities in different parts of the body, such as the neck, back, leg, arm, etc.

It will also be understood that the apparatus 10, when specifically constructed for use in detecting cancers or other abnormalities on different parts of the body, may have different threshold values stored in the memory consistent with the body part being checked. Such threshold values may differ from the threshold values described above which are used, by example, in detecting breast cancer.

Figure 5:
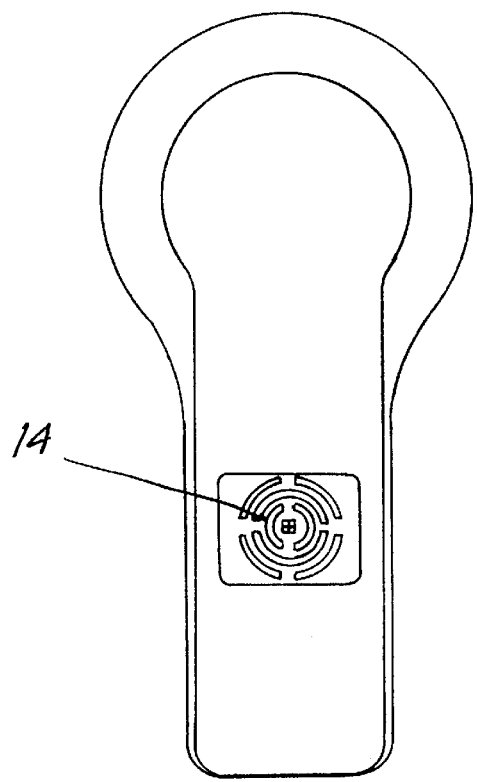
FIG. 5 is a rear elevational view of the apparatus with an acoustic output device.

The output device may also be an acoustical device 14 shown in FIG. 5 which is able to produce three different tones, one for each distinct condition. The acoustical device 14 may be any sound generating device capable of producing multiple tones or, alternately, a single tone which is capable of being generated in different sequences, such as a constant tone and varying at different frequencies to be able to be distinctly detected as each distinct condition.

It will also be understood that the apparatus may be constructed with any combination of the three different output devices 6 discussed above or equivalents.

When the sensing surface 1 of the apparatus is gently pressed against the skin, taking care that the center detector 2 is as close as possible above the point of clinical interest to be analyzed, the signal processor 5 calculates the temperature difference between each of the thermal detectors 3 and the central detector 2. The highest obtained value is stored in the memory.

The procedure can be repeated by applying the apparatus again on the same skin surface or by repositioning it to a different location on the skin surface. If so, a new highest temperature difference is calculated and compared with the previous highest temperature difference. The highest of the two is stored in the memory. Finally this value is compared with two stored threshold temperature differences.

If the threshold temperature difference is less than the first threshold, the first output device 6 is activated, i.e., the green LED 11 is lit, or the first acoustic tonality is produced, or the luminous point 13 in the display 12 is not lit.

If the temperature difference is larger than the first threshold, but does not exceed the second threshold, the second level of output is activated, i.e., the yellow light 10 is lit, or the point 13 flashes on display 12, or the second acoustic tonality is emitted.

If the second threshold is surpassed, the signal meaning abnormal is activated, i.e., the red LED 6 is lit, or the point 13 steadily lit on the display 12, or the third tonality is emitted.

Should the doubtful case occur, the person using the apparatus becomes aware that a new test must be performed soon. Should the abnormal case occur, the tested person becomes aware that more complex medical analyses must be performed, probably in a medical laboratory.

What is claimed is:

1. An apparatus for monitoring a temperature of a region of human tissue, the apparatus comprising:
   a sensing surface;
   a plurality of detector means, including a center detector means and at least two additional detector means spaced equidistantly from the center detector means and carried on the sensing surface, for sensing a skin temperature when the sensing surface is placed in proximity with human skin;

means, responsive to the detector means, for determining the highest temperature difference between each of the at least two additional detector means and the center detector means;

means for comparing the highest determined temperature difference with at least one threshold temperature; and means, responsive to the comparing means, for generating at least one output corresponding to the relationship of the highest determined temperature difference to the at least one threshold temperature.

2. The apparatus of claim 1 wherein the detector means comprises near infrared temperature detectors.

3. The apparatus of claim 1 wherein the detector means comprises thermistors.

4. The apparatus of claim 1 wherein the at least one output comprises a plurality of light emitting diodes, one light emitting diode corresponding to a distinct temperature range with respect to the at least one threshold temperature.

5. The apparatus of claim 1 wherein the at least one output comprises an illuminatable graphical display.

6. The apparatus of claim 1 wherein the at least one output comprises acoustic means for generating a plurality of distinct sounds, each corresponding to a distinct temperature range with respect to the threshold temperature.

7. The apparatus of claim 1 wherein the at least one threshold temperature comprises first and second distinct threshold temperatures.

8. The apparatus of claim 7 wherein the at least one output comprises:

three distinct outputs including a first output corresponding to the highest determined temperature being lower than the first threshold temperature, a second output corresponding to the highest determined temperature between the first and second threshold temperature, and a third output corresponding to the highest determined temperature being greater than the second threshold temperature.

9. The apparatus of claim 8 wherein the three distinct outputs comprise three distinct illuminatable means for indicating three distinct output states, respectively.

10. The apparatus of claim 8 wherein the three distinct outputs comprise sound generating means for generating three distinct tones.

11. The apparatus of claim 8 wherein the three distinct outputs comprise a graphical display having an illuminatable light which is capable of three distinct light patterns.

12. A method of monitoring a temperature of a region of human tissue utilizing the apparatus of claim 1 and comprising the steps of:

determining the output of each of the at least two additional detector mean and the center detector means;

calculating the highest temperature difference between each of the at least two additional detector means and the center detector means;

comparing the highest determined temperature difference with a temperature threshold; and activating the means for generating the at least one output to indicate the relationship of the highest temperature difference and the threshold temperature.

13. The method of claim 12 further comprising the steps of:

providing at least two distinct temperature thresholds defining three distinct temperature ranges; and generating the at least one output in three distinct output states, each output state corresponding to one of the three temperature ranges formed by the at least two threshold temperatures.

* * * * *